(12) United States Patent
Prabhakar et al.

(10) Patent No.: US 10,018,804 B2
(45) Date of Patent: Jul. 10, 2018

(54) APPARATUS AND METHOD FOR MULTIPLE MODE IMAGE ACQUISITION FOR IRIS IMAGING

(71) Applicants: DELTA ID INC., Fremont, CA (US); Salil Prabhakar, Fremont, CA (US); Valentine Dvorovkin, Santa Cruz, CA (US)

(72) Inventors: Salil Prabhakar, Fremont, CA (US); Valentine Dvorovkin, Santa Cruz, CA (US)

(73) Assignee: Delta ID, Inc., Fremont, CA (US)

( * ) Notice: Subject to any disclaimer, the term of this patent is extended or adjusted under 35 U.S.C. 154(b) by 0 days.

(21) Appl. No.: 14/899,672

(22) PCT Filed: Jun. 18, 2014

(86) PCT No.: PCT/US2014/042836
§ 371 (c)(1),
(2) Date: Dec. 18, 2015

(87) PCT Pub. No.: WO2014/205021
PCT Pub. Date: Dec. 24, 2014

(65) Prior Publication Data
US 2016/0134791 A1   May 12, 2016

Related U.S. Application Data

(60) Provisional application No. 61/836,444, filed on Jun. 18, 2013.

(51) Int. Cl.
*G02B 13/00* (2006.01)
*A61B 5/1171* (2016.01)
(Continued)

(52) U.S. Cl.
CPC ........ *G02B 13/0015* (2013.01); *A61B 3/1216* (2013.01); *A61B 5/1171* (2016.02);
(Continued)

(58) Field of Classification Search
CPC .. G02B 13/0015; G02B 5/208; A61B 3/1216; A61B 5/117; G06K 9/00604;
(Continued)

(56) References Cited

U.S. PATENT DOCUMENTS 8,437,513 B1   5/2013   Derakhshani et al.
2010/0290668 A1   11/2010   Friedman et al.
(Continued)

FOREIGN PATENT DOCUMENTS

WO   98/08439   3/1998

OTHER PUBLICATIONS

Extended European Search Report issued in corresponding European Patent Application No. 14814311.8 dated Dec. 22, 2016.

*Primary Examiner* — Amandeep Saini
(74) *Attorney, Agent, or Firm* — Budzyn IP Law, LLC

(57) ABSTRACT

The invention comprises an imaging apparatus housed within a mobile device housing, and configured to enable multiple image acquisition modes. The apparatus includes an image sensor, a first optical assembly, a second optical assembly and a controller. The first optical assembly of the invention is positioned over a first image capture region of the imaging surface, and defines a first field of view—such that the first optical assembly images onto the first image capture region, any object plane within the first field of view. The second optical assembly is positioned over a second image capture region of the imaging surface, and defines a second field of view—such that the second optical assembly images onto the second image capture region, any object plane within the second field of view. The invention addi- (Continued)

tionally includes a corresponding method for enabling multiple image acquisition modes in an imaging apparatus.

14 Claims, 6 Drawing Sheets

(51) Int. Cl.
    *A61B 3/12* (2006.01)
    *G06K 9/00* (2006.01)
    *H04N 5/225* (2006.01)
    *H04N 5/232* (2006.01)
    *G02B 5/20* (2006.01)
    *A61B 5/117* (2016.01)

(52) U.S. Cl.
    CPC ......... *G02B 5/208* (2013.01); *G06K 9/00604* (2013.01); *G06K 9/00617* (2013.01); *H04N 5/2254* (2013.01); *H04N 5/23212* (2013.01); *H04N 5/23245* (2013.01); *A61B 5/117* (2013.01)

(58) Field of Classification Search
    CPC ............. G06K 9/00617; H04N 5/2254; H04N 5/23212; H04N 5/23245
    USPC ......................................................... 382/117
    See application file for complete search history.

(56) References Cited

U.S. PATENT DOCUMENTS

| | | | |
|---|---|---|---|
| 2012/0102332 A1 | 4/2012 | Mullin | |
| 2012/0200689 A1* | 8/2012 | Friedman | G06K 9/00255 348/78 |
| 2013/0051631 A1* | 2/2013 | Hanna | G06K 9/00604 382/117 |

* cited by examiner

APPARATUS AND METHOD FOR MULTIPLE MODE IMAGE ACQUISITION FOR IRIS IMAGING

CROSS-REFERENCE TO RELATED APPLICATIONS

This application is a National Stage Application under 35 U.S.C. § 371 of PCT Application No. PCT/US2014/042836, filed on Jun. 18, 2014, which claims priority to U.S. Provisional Patent Application No. 61/836,444, filed on Jun. 18, 2013, the entire contents of which are incorporated by reference herein.

FIELD OF INVENTION

The invention relates to an imaging apparatus and method, which imaging apparatus and method enables obtaining images of one or more features of a subject's eye for biometric identification. The invention is particularly operable to obtain images in a first mode and in a second mode, wherein at least the first image acquisition mode is optimized for iris image capture for the purposes of iris recognition.

BACKGROUND

Methods for biometric identification based on facial features, including features of the eye are known. Methods for iris recognition implement pattern-recognition techniques to compare an acquired image of a subject's iris against a previously acquired image of the subject's iris, and thereby determine or verify identity of the subject. A digital template corresponding to an acquired iris image is encoded based on the image, using mathematical/statistical algorithms. The digital template is compared against databases of previously encoded digital templates (corresponding to previously acquired iris images), for locating a match and thereby determining or verifying identity of the subject.

Apparatuses for iris recognition may comprise an imaging apparatus for capturing an image of the subject's iris(es) and an image processing apparatus for comparing the captured image against previously stored iris image information. The imaging apparatus and image processing apparatus may comprise separate devices, or may be combined within a single device.

While iris recognition apparatuses have been previously available as dedicated or stand alone devices, it is increasingly desirable to incorporate iris recognition capabilities into mobile communication devices or mobile computing devices (collectively referred to as "mobile devices") having inbuilt cameras, such as for example, mobile phones, smart phones, personal digital assistants, tablets or laptop devices.

It has however been found that cameras within mobile devices are intended to operate as general purpose cameras, capable of capturing images of objects situated at a wide range of distances from the mobile device. The considerations for acquiring iris images for the purpose of biometric recognition, are significantly different from considerations applicable to image capture of non-iris images. Specifically, iris imaging particularly necessitates positioning of a subject's iris within a defined image capture region, such that the iris image acquired by the imaging apparatus satisfies a minimum pixel resolution in the object plane. Given the size of the iris, and pixel size of image sensors typically used in mobile device cameras, configuring a camera to capture an iris image having suitable iris diameter in the image plane, requires a specific object distance (i.e. distance at which the subject's iris requires to be positioned) and/or changing magnification (and therefore focal length) of the camera. Configuring a camera inbuilt into a mobile device in this manner may render the camera unsuitable for multiple uses (such as for iris imaging as well as video conferencing, video recording or photography purposes) while maintaining image sharpness and detail.

Prior art solutions for altering an object plane of a camera typically involve a zoom lens type arrangement, where the lens assembly comprises a number of individual lenses that may slide axially along the body of the lens assembly to change focal length and magnification of the lens assembly. However, zoom lenses are expensive and bulky, both of which provide serious disincentives for use in cameras inbuilt into mobile devices.

Another concern that arises from dual use of fixed focus cameras, is that iris image capture typically relies on infrared (IR) wavelengths, whereas non-iris image capture usually seeks to eliminate IR wavelengths by using IR cut filters (filters which reflect or absorb IR wavelengths, while allowing visible wavelengths to pass through the lens assembly and on to the image sensor).

It is therefore an objective of the invention to provide efficient and cost effective mechanisms to configure a camera built into a mobile device such that the camera can switch between multiple modes of image capture, wherein each of the multiple modes alters one or more of, the object distance, image distance, camera's field of view, depth of field, and optical filtering properties of the camera.

SUMMARY

The invention comprises an imaging apparatus housed at least partially within a mobile device housing, and configured to enable multiple image acquisition modes. The imaging apparatus includes an image sensor comprising an imaging surface, a first optical assembly, a second optical assembly and a controller.

The first optical assembly of the invention may be positioned over a first image capture region of the imaging surface, and may define a first field of view—such that the first optical assembly images onto the first image capture region, any object plane within the first field of view. The second optical assembly may be positioned over a second image capture region of the imaging surface, and may define a second field of view—such that the second optical assembly images onto the second image capture region, any object plane within the second field of view. The first optical assembly and second optical assembly of the imaging apparatus may be integrally formed. In an embodiment of the invention, imaging surfaces respectively underlying the first image capture region and the second image capture region may be discretely formed.

Each of the first optical assembly and the second optical assembly comprise at least one of a lens or an optical filter. The first optical assembly may be interpositioned between the first image capture region and a third optical assembly that is non-substitutably interposed between the image sensor and the first and second fields of view. Alternatively, the second optical assembly may be interpositioned between the second image capture region and the third optical assembly.

In an embodiment, the first optical assembly may be configured to confer upon the imaging apparatus, a first set of image capture properties corresponding to the first field of view. The first set of image capture properties may differ from a second set of image capture properties conferred upon the imaging apparatus by the second optical assembly corresponding to the second field of view. In a specific embodiment, the first set of image capture properties may differ from the second set of image capture properties on the basis of one or more of field of view, focus, focal length, depth of field, optical filtering properties, magnification, modulation transfer function (MTF), position of a principal plane of an optical assembly, or position of a focal plane of an optical assembly.

The first optical assembly or the second optical assembly of the imaging apparatus may comprise one or more of an infra-red pass filter, a narrow band filter, an infra-red cut filter, a refractive optical element, or a plano-parallel refractive element.

The controller within the imaging apparatus may be configured to process image data from pixels within the first image capture region responsive to triggering of a first image capture mode, and to process image data from pixels within the second image capture region responsive to triggering of a second image capture mode. The controller may be located at least partially outside the mobile device housing. The controller may be configured to selectively process image data from within the first image capture region or the second image capture region during any one of image capture, image parsing or image rendering.

The controller may be configured to respond to triggering of the first image capture mode by processing a first set of image data acquired from pixels within the first image capture region, and a second set of image data acquired from pixels within the second image capture region. An image based on one of the first set of image data and the second set of image data from pixels may be rendered by the controller for display. Thereafter the other of the first set of image data and the second set of image data may be used for comparing iris information within such first or second set of image data with stored iris information corresponding to at least one iris, and for rendering a match decision or a non-match decision based on an output of the comparison. In a specific embodiment of the invention, the image thus rendered for display to an operator enables the operator to optimize image capture parameters for iris imaging.

In an embodiment of the invention, the first image capture mode or the second image capture mode may be respectively triggered responsive to an object of interest being positioned within the first field of view or the second field of view. At least one of the first image capture mode and second image capture mode may be optimized for iris imaging.

In a particular embodiment of the invention, the first image capture region and the second image capture region may be separated by a transition region, wherein pixel data from within the transition region is disregarding during image capture, image parsing or image rendering.

In an embodiment of the invention, the imaging apparatus may comprise a camera disposed within a housing of any one of a mobile telecommunication device.

In another embodiment, the invention may comprise a method for enabling multiple image acquisition modes in an imaging apparatus, wherein the imaging apparatus is housed at least partially within a mobile device housing. The method may comprise (i) defining for an image sensor comprising an imaging surface, a first image capture region and a second image capture region within the imaging surface (ii) positioning a first optical assembly over the first image capture region, wherein the first optical assembly defines a first field of view and images onto the first image capture region, any object plane within the first field of view (iii) positioning a second optical assembly over the second image capture region, wherein the second optical assembly defines a second field of view and images onto the second image capture region, any object plane within the second field of view and (iv) configuring a controller to (a) process image data from pixels within the first image capture region responsive to triggering of a first image capture mode, and (b) process image data from pixels within the second image capture region responsive to triggering of a second image capture mode.

The method embodiments of the invention may include some or all of the limitations discussed above in connection with the apparatus embodiment.

BRIEF DESCRIPTION OF THE ACCOMPANYING DRAWINGS

DETAILED DESCRIPTION

Figure 1:
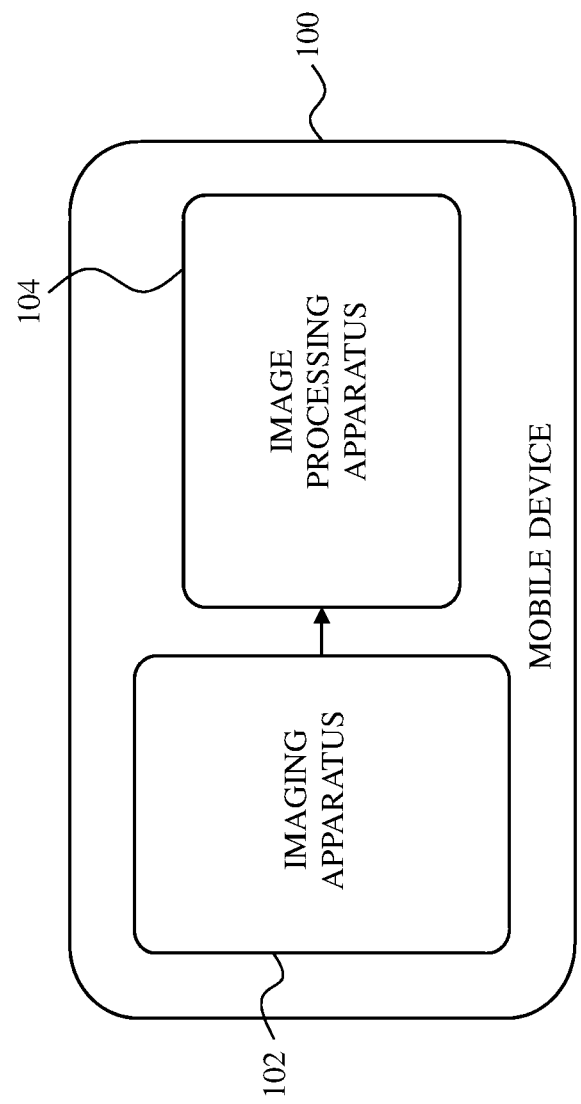
FIG. 1 is a functional block diagram of a mobile device configured for iris image based recognition.

FIG. 1 is a functional block diagram of a mobile device 100 configured for iris image based recognition, comprising an imaging apparatus 102 and an image processing apparatus 104. Imaging apparatus 102 acquires an image of the subject's iris and transmits the image to image processing apparatus 104. The image captured by imaging apparatus 102 may be a still image or a video image. Image processing apparatus 104 thereafter analyses the acquired image frame(s) and compares the corresponding digital feature set with digital templates encoded and stored based on previously acquired iris images, to identify the subject, or to verify the identity of the subject.

Although not illustrated in FIG. 1, mobile device 100 may include other components, including for extracting still frames from video images, for processing and digitizing image data, for enrolment of iris images (the process of capturing, and storing iris information for a subject, and associating the stored information with that subject) and comparison (the process of comparing iris information acquired from a subject against information previously acquired during enrolment, for identification or verification of the subject's identity), and for enabling communication between components of the mobile device. The imaging apparatus, image processing apparatus and other components of the mobile device may each comprise separate devices, or may be combined within a single mobile device.

Figure 2:
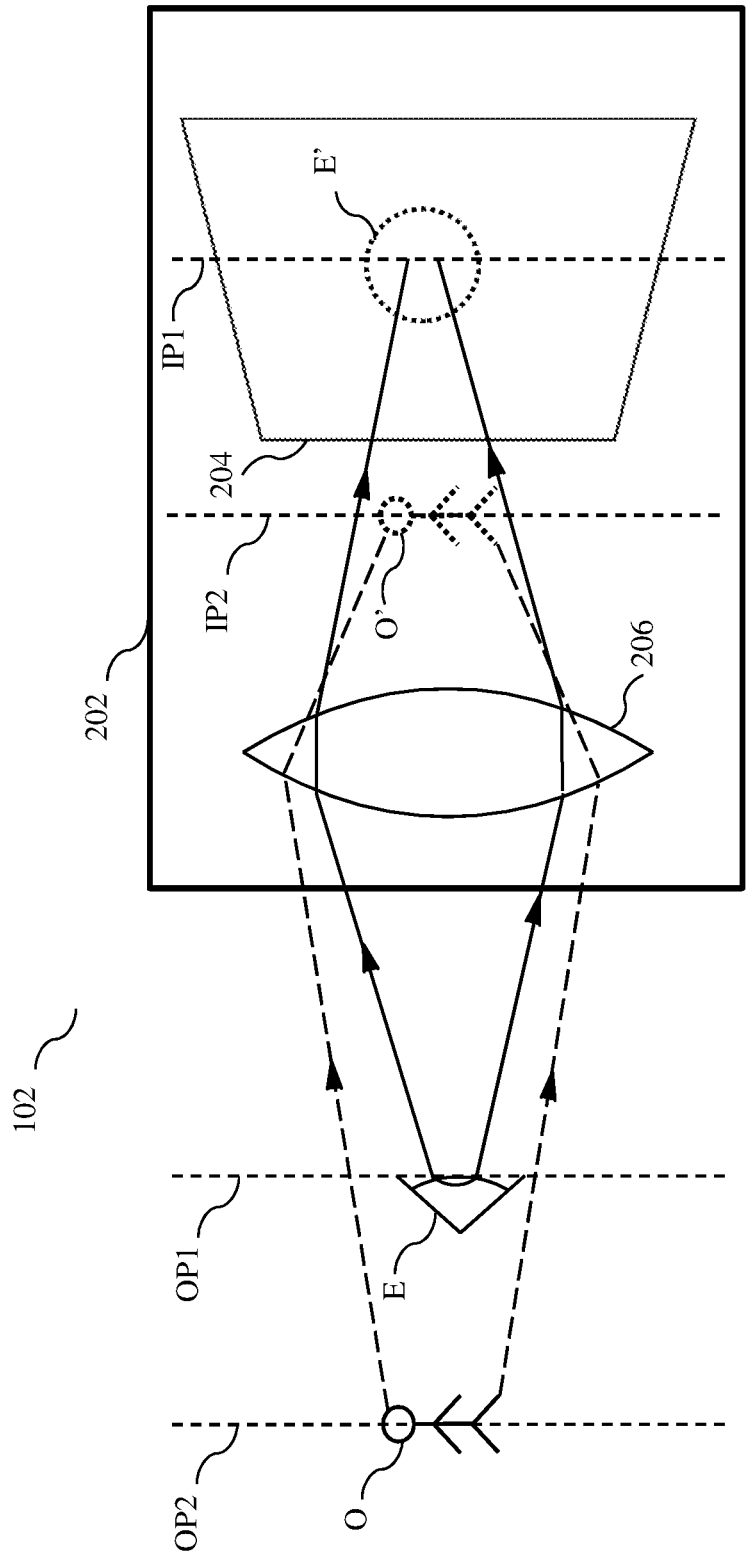
FIG. 2 illustrates an exemplary embodiment of the imaging apparatus.

FIG. 2 illustrates an exemplary embodiment of imaging apparatus 102 having housing 202, image sensor 204 and an optical assembly 206, wherein image sensor 204 and optical assembly 206 are disposed within the housing 206.

Imaging apparatus 102 may comprise a conventional solid state still camera or video camera, and image sensor 204 may comprise a charged coupled device (CCD) or a complementary metal oxide semiconductor (CMOS) device. Image sensor 204 may be selected for sensitivity at least to light having wavelengths anywhere in the range of 400 nanometres to 1000 nanometres. Optical assembly 206 may comprise an integrally formed or single unitarily formed element, or may comprise an assembly of optical elements selected and configured for achieving desired image forming properties. The imaging apparatus as illustrated has a fixed focus, of a type that is conventionally disposed within mobile devices.

The illustration in FIG. 2 exemplifies a problem faced in adapting fixed focus cameras to a dual use configuration, for enabling iris imaging as well as general photography. As shown in FIG. 2, optical assembly 206 and image sensor 204 may be configured and disposed relative to each other, such that when a subject's eye E is positioned at object plane OP1, an in-focus image E' of the eye is formed at image plane IP1, which image plane coincides with an imaging surface of image sensor 204. On the other hand, given the fixed focus configuration of the illustrated imaging apparatus, when an object O is positioned at object plane OP2 (which object plane OP2 is located further away from the imaging apparatus in comparison to object plane OP1), an image O' of the object is formed at image plane IP2, which image plane does not coincide with the imaging surface of image sensor 204—and thereby causes an out-of-focus image to acquired by image sensor 204.

Figure 3:
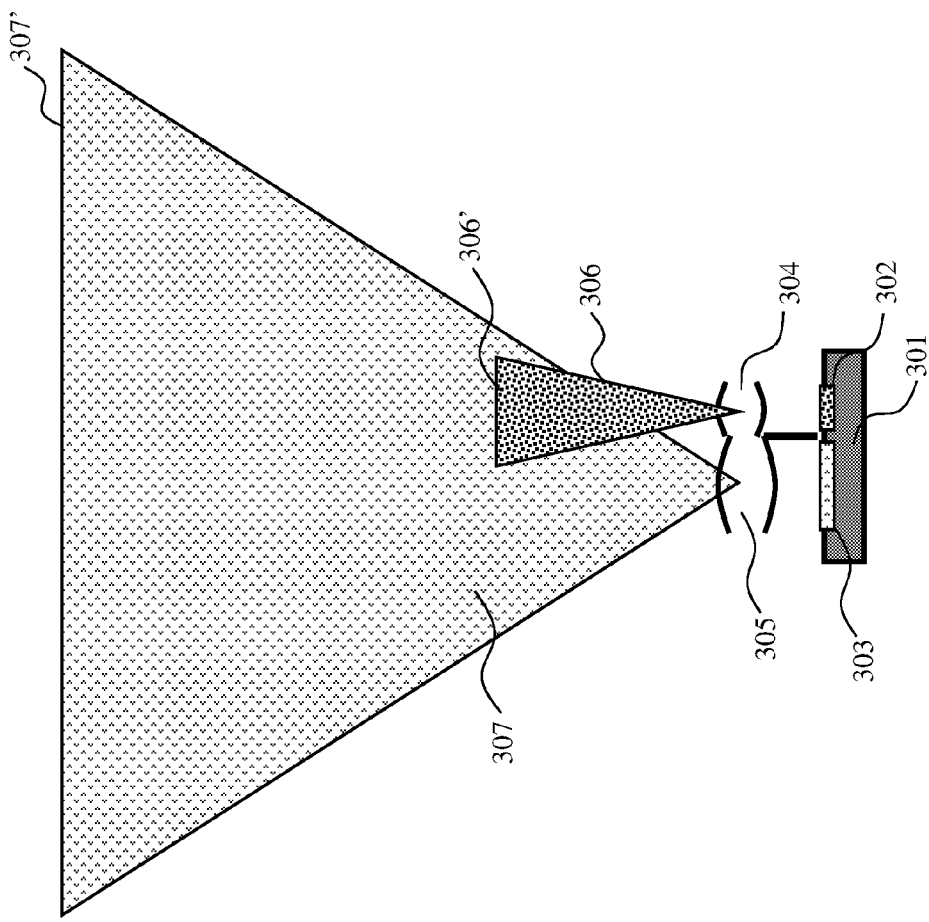
FIGS. 3, 3A and 4 illustrate embodiments a dual mode imaging apparatus.
Figure 4:
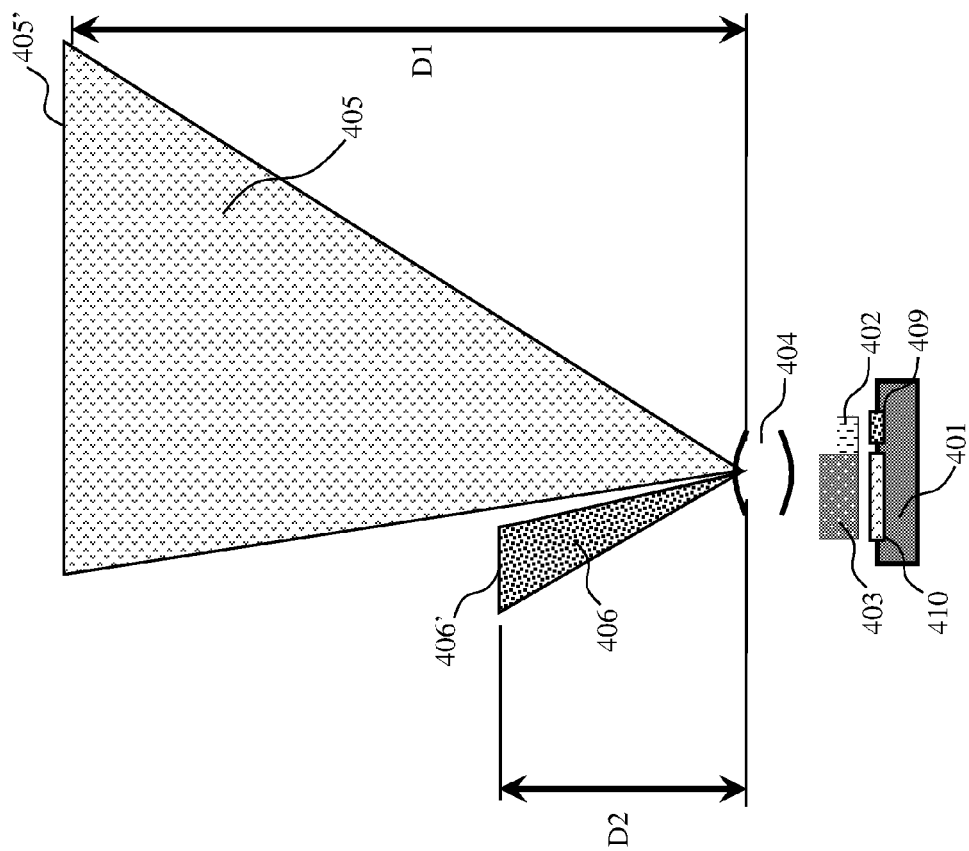

The present invention seeks to provide a solution to the above problems by providing an imaging apparatus capable of alternating between two or more image capture configurations or modes, without recourse to moving parts. FIGS. 3 and 4 illustrate exemplary embodiments of the invention.

FIG. 3 illustrates a dual mode camera configuration, wherein image sensor 301 comprises a first image capture region 302 and a second image capture region 303. Positioned between image sensor 301 and intended object positions are first optical assembly 304 and second optical assembly 305. As illustrated, first optical assembly 304 is interposed in front of first image capture region 302 of image sensor 301, and second optical assembly 305 is interposed in front of second image capture region 303 of image sensor 301. The first optical assembly 304 and second optical assembly 305 may be selected such that they each have different working distance and/or have different magnification and/or have different optical filtering properties.

The first optical assembly 304 may configured and selected to have a first field of view 306 and a first object plane 306', while the second optical assembly 305 may be configured and selected to have a second field of view 307 and optionally a second object plane 307' and depth of field. The first and second optical assemblies are positioned relative to the image sensor such that the image of an object positioned within the first field of view 306 and at the first object plane 306' will be projected on to the first image capture region 302 of image sensor 301, while images of objects positioned within the second field of view 307 will be projected on to the second image capture region 303 of image sensor 301. In an embodiment, first optical assembly 304 may be configured such that object plane 306' is selected to be appropriate for iris image capture, while second optical assembly 305 may be configured to satisfy constraints optimal for non-iris image capture (such as for example for general purpose photography).

Since images of objects positioned within one image capture region 306 are formed on a first part 302 of image sensor 301, and images of objects positioned within a second image capture region 307 are formed on a second part 303 of the image sensor 301, the invention can selectively record information depending on whether the camera is in a first image capture mode or in a second image capture mode.

In an embodiment of the invention, responsive to triggering of the first image capture mode, image data from pixels within first image capture region 302 is parsed and used while image data from second image capture region 303 is ignored. Responsive to triggering of the second image capture mode, image data from pixels in second image capture region 303 is parsed and used while image date from first image capture region 302 is ignored.

In another embodiment of the invention, responsive to triggering of the first image capture mode, a first set of image data comprising image data from pixels within first image capture region 302 is processed along a second set of image data comprising image data from pixels within second image capture region 303. An image based on one of the first set of image data and the second set of image data is rendered for display to an operator of the imaging apparatus, while the other of said first or second set of image data may be utilized for comparing iris information within said image data set with stored iris information corresponding to at least one iris, and thereafter rendering a match or non-match decision based on output of such comparison. In a more particular embodiment, the image rendered for display enables the operator to optimize image capture parameters (such as for example, position of the subject's eye, illumination, orientation of the imaging apparatus or mobile device) for iris imaging.

In a specific embodiment of the invention, the first image capture mode or the second image capture mode may be triggered responsive to an object of interest (such as for example a subject's iris) being positioned within the first field of view or the second field of view. Either of the first image capture mode or the second image capture mode may be optimized for iris imaging.

Switching between modes and selective parsing of pixel data may be accomplished directly by appropriate assertion of control signals by a controller, control circuitry or by a processor during pixel readout. Equally, selective parsing may be accomplished subsequently after all image data is read from the pixel array, or may even be achieved by imaging software after image rendering. The controller, control circuitry or processor for switching between modes and selective parsing of pixel data may in an embodiment be located at least partially outside the mobile device housing.

Figure 3A:
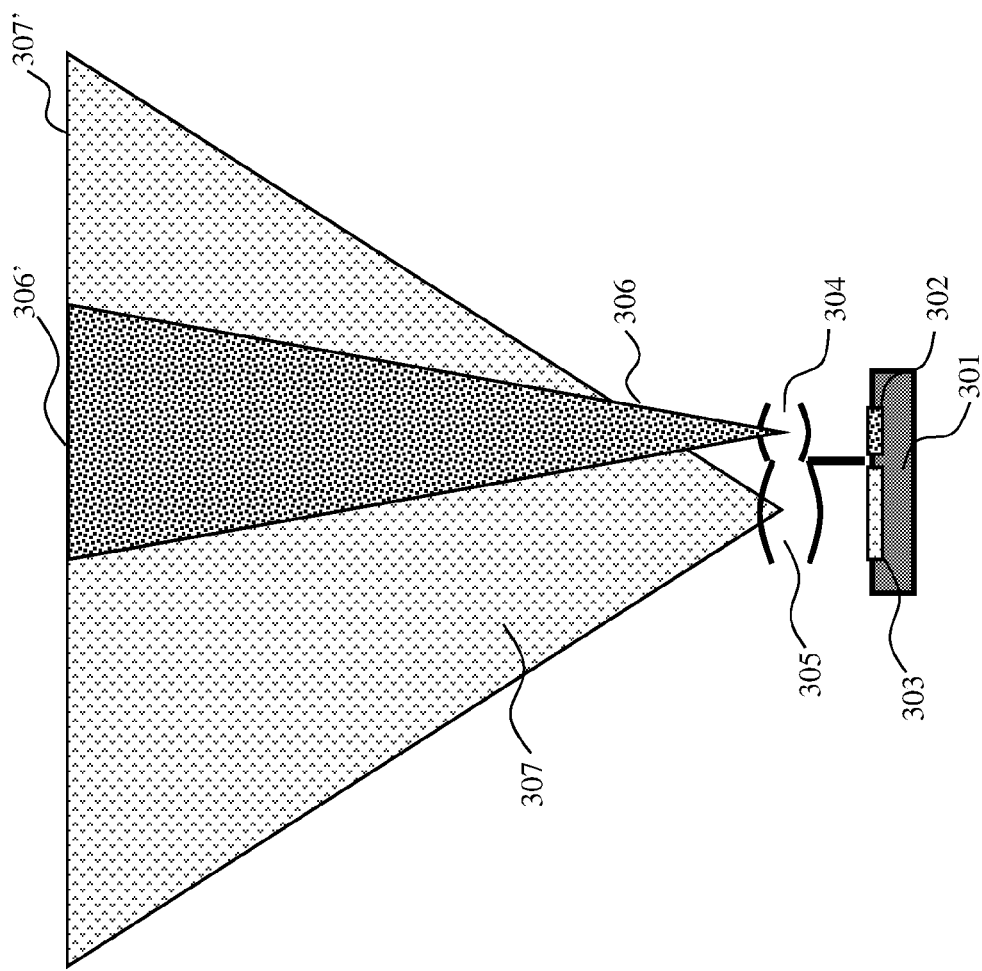

FIG. 3A illustrates an alternative embodiment of the dual mode camera configuration, illustrated in FIG. 3, wherein first optical assembly 304 and second optical assembly 305 are respectively interposed in front of first image capture region 302 of image sensor 301, and second image capture region 303 of image sensor 301 such that they both have the same working distance (i.e. their respective object planes 306' and 307' are at the same distance from the image sensor, thereby configuring both first image capture region 302 and second image capture region 303 for acquiring in-focus images of objects positioned at the same object plane). As illustrated in FIG. 3A, despite having the same working distance, optical assemblies 304 and 305 may be configured to provide different angular fields of view and/or resolution, for image acquisition. Other differences between optical assemblies 304 and 305 may include magnification and/or optical filtering properties. In a specific embodiment of the configuration illustrated in FIG. 3A, second optical assembly 305 may be configured for acquiring for image processing, an image of a subject's face positioned at object plane 307', while first optical assembly 304 may be configured for acquiring for image processing, and image of the subject's eye or iris, positioned within the narrower angular field of view of first optical assembly 304.

While the embodiment illustrated in FIG. 3 shows two discrete optical assemblies 304 and 305, it will be understood that the two optical assemblies can be integrated into a integrally formed or unitary element having two optical regions, each region having configurations corresponding to the optical assemblies 304 and 305.

In another embodiment of the invention, the mobile device may have only a single optical assembly, but may have multiple refractive optical elements (such as plano-parallel optical elements), interposed between the image sensor and the optical assembly, each refractive optical element having a different thickness or refractive index or both—and which refractive optical elements serve to alter the effective image distance of the optical assembly.

FIG. 4 illustrates another embodiment of a dual mode camera configuration. Positioned between image sensor 401 and the intended object positions are optical assembly 404. As illustrated, a first refractive optical element 402 is interposed between optical assembly 404 and a first region 409 of image sensor 401. A second refractive optical element 403 is interposed between optical assembly 404 and a second region 410 of image sensor 401. The first and second refractive optical elements 402 and 403 may respectively be configured such that they differentially alter the image distance of the optical assembly without altering the focal length of the lens assembly or the image plane (position of the image sensor relative to the lens assembly). Accordingly, first refractive optical element 402 effects a first image distance for the optical assembly 404 while second refractive optical element 403 effects a second image distance for the optical assembly 404.

As illustrated in FIG. 4, refractive optical element 403 effects a first image distance for the optical assembly such that, when an object is positioned within field of view 405 and at distance D1 from image sensor 401, an in-focus image of the object is formed on the second part 410 of image sensor 401. Similarly, refractive optical element 402 is configured to effect a second image distance for the optical assembly such that, when an object is positioned within field of view 406 and at distance D2 from image sensor 401, an in-focus image of the object is formed on the first part 409 of image sensor 401. In a preferred embodiment, one of the refractive optical elements is specifically configured to ensure an appropriate image distance for iris image capture.

While the embodiment illustrated in FIG. 4 shows two refractive optical elements 402 and 403, it will be understood that the same effect may be achieved by having only a single refractive optical element interposed between the optical assembly 404 and a first image capture region of the image sensor, while the second image capture region of the image sensor and optical assembly 404 does not have any refractive optical element interposed therebetween. In this specific embodiment, the optical assembly 404 is configured to form an in-focus image of an object at a first object plane, on a first region of the image sensor, while the optical assembly in combination with the refractive optical element forms an in-focus image of an object at a second object plane, on a second region of the image sensor.

Optionally, the optical assembly and refractive optical elements may be positioned so as to have a transition area—wherein for image clarity, images of objects positioned within the transition area are disregarded during image capture or image parsing or image rendering. It would however be understood that embodiments without a transition area are entirely implementable as well.

Since images of objects positioned within one image capture region 405 are formed on a first part of image sensor 401, and images of objects positioned within a second image capture region 406 are formed on a second part of the image sensor 401, the invention can selectively record information depending on whether the camera is in a first image capture mode or in a second image capture mode. In the illustrated embodiment, in the first image capture mode, image data from pixels within the first image capture region may be used while image data from second image capture region is ignored. In the second image capture mode, image data from pixels in the second image capture region is used while image date from the first image capture region is ignored. Switching between modes and selective parsing of pixel data may be accomplished directly by appropriate assertion of control signals by control circuitry during pixel readout. Equally, selective parsing may be accomplished subsequently after all image data is read from the pixel array, or may even be achieved by imaging software after image rendering.

It will be understood that the two refractive optical elements 402 and 403 may be discrete elements or can be integrated into a unitary element having two optical regions, each region having configurations corresponding to the optical elements 402 and 403.

By selectively recording an image received through an appropriately configured refractive optical element (such as the plano-parallel element) within the imaging apparatus an appropriate refractive optical element, the object plane may be altered without altering focal length of the lens assembly or the image plane (position of the image sensor).

The first and second optical assemblies of FIGS. 3, 3A and 4 may each comprise at least one of a lens or an optical filter. In an embodiment of the invention, the first optical assembly may be interpositioned between the first image capture region and a third optical assembly. Alternatively, the second optical assembly may be interpositioned between the second image capture region and third optical assembly. The third optical assembly may be non-substitutably interposed between the image sensor and the first and second fields of view.

The first optical assembly may be configured to confer upon the imaging apparatus, a first set of image capture properties corresponding to the first field of view. The second optical assembly may be configured to confer upon the imaging apparatus, a second set of image capture properties corresponding to the second field of view. The first set of image capture properties may differ from the second set of image capture properties—and in an embodiment, may differ on the basis of one or more of field of view, focus, focal length, depth of field, optical filtering properties, magnification, modulation transfer function (MTF), position of a principal plane of an optical assembly, or position of a focal plane of an optical assembly.

In an embodiment of the invention, the first optical assembly or the second optical assembly may comprise one or more of an infra-red pass filter, a narrow band filter, an infra-red cut filter, a refractive optical element, or a plano-parallel refractive element.

While the image sensor of FIGS. 3, 3A and 4 have been illustrated as a unitary image sensor having a first and second image capture region, the same function may equally be achieved by integrating or positioning more than one discretely formed image sensors adjacent to each other. Additionally, while the illustrated embodiments each show components for two image capture modes, the invention equally contemplates more than two image capture modes by adding additional optical assemblies or additional refractive optical elements or additional image sensors.

In preferred embodiments, each of the above arrangements for dual mode image capture may be used to switch between iris image capture mode and non-iris image capture mode. However, the above arrangements are not limited in application to switching between iris image capture and non-iris image capture, and may instead be used to configure a mobile device camera to switch between any two or more different image capture modes which are capable of being achieved by changing one or more of object distance, image distance, focal length, field of view, depth of field or filtering properties.

Figure 5:
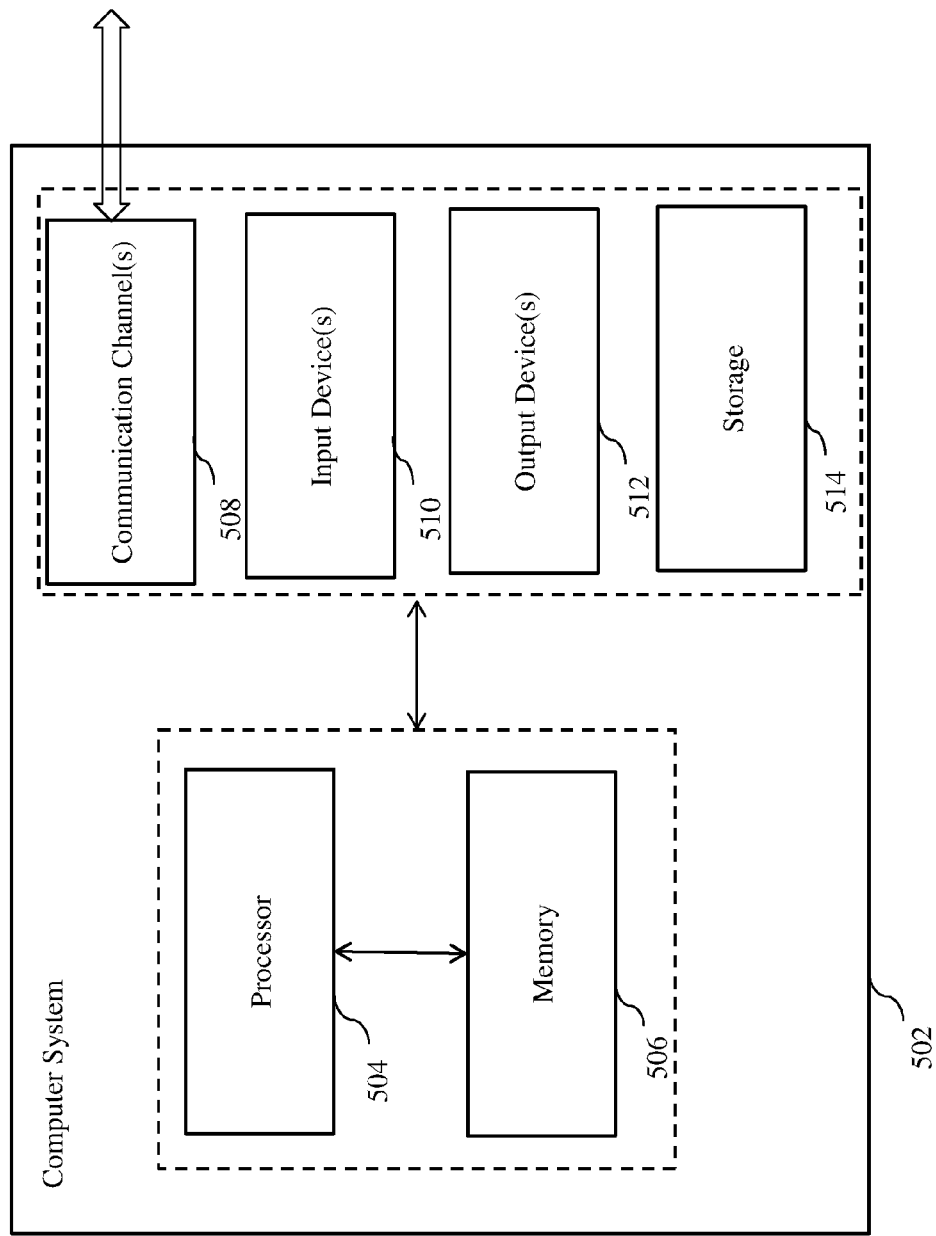
FIG. 5 illustrates an exemplary processing system for the image processing apparatus.

FIG. 5 illustrates an exemplary processing system in which various embodiments of the image processing apparatus of FIG. 1, or the control processor discussed in connect in with FIGS. 3 and 4 may be implemented.

The system 502 comprises at-least one processor 504 and at-least one memory 506. The processor 504 executes program instructions and may be a real processor. The processor 504 may also be a virtual processor. The computer system 502 is not intended to suggest any limitation as to scope of use or functionality of described embodiments. For example, the computer system 802 may include, but not limited to, one or more of a general-purpose computer, a programmed microprocessor, a micro-controller, an integrated circuit, and other devices or arrangements of devices that are capable of implementing the steps that constitute the method of the present invention. In an embodiment of the present invention, the memory 506 may store software for implementing various embodiments of the present invention. The computer system 502 may have additional components. For example, the computer system 502 includes one or more communication channels 508, one or more input devices 510, one or more output devices 512, and storage 514. An interconnection mechanism (not shown) such as a bus, controller, or network, interconnects the components of the computer system 802. In various embodiments of the present invention, operating system software (not shown) provides an operating environment for various softwares executing in the computer system 502, and manages different functionalities of the components of the computer system 502.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims.

The invention claimed is:

1. An imaging apparatus housed at least partially within a mobile device housing, and configured for multiple image acquisition modes, the imaging apparatus comprising:
    an image sensor comprising an imaging surface;
    a first optical assembly positioned over a first image capture region of the imaging surface, and defining a first field of view, said first image capture region of the imaging surface including a first set of image sensor pixels therewithin, wherein the first optical assembly images onto the first image capture region, any object plane within the first field of view; and
    a second optical assembly positioned over a second image capture region of the imaging surface, and defining a second field of view, said second image capture region of the imaging surface including a second set of image sensor pixels therewithin, wherein the second optical assembly images onto the second image capture region, any object plane within the second field of view, and wherein the first and second image capture regions are mutually distinguishable regions on the imaging surface;
    a processor configured to:
        respond to detection of a first trigger event that has been defined to trigger a first image capture mode, by performing an image display on a display screen, wherein performing the image display on the display screen comprises:
            parsing image data from the first set of image sensor pixels; and
            rendering an image on the display screen, wherein the rendered image is based on the image data parsed from the first set of image sensor pixels; and
        respond to detection of a second trigger event that has been defined to trigger a second image capture mode, by performing iris based biometric authentication, wherein performing said iris based biometric authentication comprises:
            extracting iris information from image data parsed from the second set of image sensor pixels;
            comparing the extracted iris information with stored iris information corresponding to at least one iris; and
            rendering one of a match decision or a non-match decision based on an output of said comparison.

2. The imaging apparatus as claimed in claim 1, wherein each of the first optical assembly and the second optical assembly comprise at least one of a lens or an optical filter.

3. The imaging apparatus as claimed in claim 1, wherein the first optical assembly is interpositioned between the first image capture region and a third optical assembly that is non-substitutably interposed between the image sensor and the first and second fields of view, or the second optical assembly is interpositioned between the second image capture region and a third optical assembly that is non-substitutably interposed between the image sensor and the first and second fields of view.

4. The imaging apparatus as claimed in claim 1, wherein:
    the first optical assembly confers upon the imaging apparatus a first set of image capture properties corresponding to the first field of view, wherein the first set of image capture properties differs from a second set of image capture properties conferred upon the imaging apparatus by the second optical assembly corresponding to the second field of view; and
    the first set of image capture properties differ from the second set of image capture properties on the basis of one or more of field of view, focus, focal length, depth of field, optical filtering properties, magnification, modulation transfer function (MTF), position of a principal plane of an optical assembly, or position of a focal plane of an optical assembly.

5. The imaging apparatus as claimed in claim 1, wherein the first optical assembly or the second optical assembly comprises one or more of an infra-red pass filter, a narrow band filter, an infra-red cut filter, a refractive optical element, or a plano-parallel refractive element.

6. The imaging apparatus as claimed in claim 1, wherein the second image capture mode is optimized for iris imaging.

7. The imaging apparatus as claimed in claim 1, wherein the first image capture region and the second image capture region are separated by a transition region, wherein pixel data from within the transition region is disregarded during image capture, image parsing or image rendering.

8. The imaging apparatus as claimed in claim 6, wherein the processor is configured to respond to triggering of the second image capture mode by:

parsing image data from the first set of image sensor pixels; and rendering an image on the display screen, wherein the rendered image is based on the image data parsed from the first set of image sensor pixels; and extracting iris information from image data parsed from the second set of image sensor pixels;

comparing the extracted iris information with stored iris information corresponding to at least one iris; and rendering one of a match decision or a non-match decision based on an output of said comparison.

9. A method for enabling multiple image acquisition modes in an imaging apparatus, wherein the imaging apparatus is housed at least partially within a mobile device housing, the method comprising:

defining for an image sensor comprising an imaging surface, a first image capture region and a second image capture region within the imaging surface;

positioning a first optical assembly over the first image capture region, wherein the first optical assembly defines a first field of view and images onto the first image capture region, any object plane within the first field of view, and wherein said first image capture region of the imaging surface includes a first set of image sensor pixels therewithin;

positioning a second optical assembly over the second image capture region, wherein the second optical assembly defines a second field of view and images onto the second image capture region, any object plane within the second field of view, and wherein said second image capture region of the imaging surface includes a second set of image sensor pixels therewithin, and wherein the first and second image capture regions are mutually distinguishable regions on the imaging surface; and configuring a processor to execute stored program instructions to:

respond to detection of a first trigger event that has been defined to trigger a first image capture mode, by performing an image display on a display screen, wherein performing the image display on the display screen comprises:

parsing image data from the first set of image sensor pixels; and rendering an image on the display screen, wherein the rendered image is based on the image data parsed from the first set of image sensor pixels; and respond to detection of a second trigger event that has been defined to trigger a second image capture mode, by performing iris based biometric authentication, wherein performing said iris based biometric authentication comprises:

extracting iris information from image data parsed from the second set of image sensor pixels;

comparing the extracted iris information with stored iris information corresponding to at least one iris; and rendering one of a match decision or a non-match decision based on an output of said comparison.

10. The method as claimed in claim 9, wherein the first optical assembly is positioned between the first image capture region and a third optical assembly that is non-substitutably interposed between the image sensor and the first and second fields of view, or the second optical assembly is positioned between the second image capture region and a third optical assembly, that is non-substitutably interposed between the image sensor and the first and second fields of view.

11. The method as claimed in claim 9, wherein:

the first optical assembly confers upon the imaging apparatus a first set of image capture properties corresponding to the first field of view, wherein the first set of image capture properties differs from a second set of image capture properties conferred upon the imaging apparatus by the second optical assembly corresponding to the second field of view; and the first and second optical assemblies are selected such that, the first set of image capture properties differ from the second set of image capture properties on the basis of one or more of field of view, focus, focal length, depth of field, optical filtering properties, magnification, modulation transfer function (MTF), position of a principal plane of an optical assembly, or position of a focal plane of an optical assembly.

12. The method as claimed in claim 9, comprising optimizing the second image capture mode for iris imaging.

13. The method as claimed in claim 12, wherein the processor is configured to respond to triggering of the second image capture mode by:

parsing image data from the first set of image sensor pixels; and rendering an image on the display screen, wherein the rendered image is based on the image data parsed from the first set of image sensor pixels; and extracting iris information from image data parsed from the second set of image sensor pixels;

comparing the extracted iris information with stored iris information corresponding to at least one iris; and rendering one of a match decision or a non-match decision based on an output of said comparison.

14. The method as claimed in claim 9, wherein defining the first image capture region and the second image capture region includes defining a transition region separating the first and second image capture regions, and configuring the processor to disregard pixel data from within the transition region during image capture, image parsing or image rendering.

* * * * *